United States Patent [19]
Shoji et al.

[11] Patent Number: 5,886,000
[45] Date of Patent: Mar. 23, 1999

[54] ANTI-HIV AGENT

[75] Inventors: Shozo Shoji, Kumamoto; Kuniomi Tachibana, Ibaraki, both of Japan

[73] Assignee: Nissui Pharmaceutical Co., Ltd,, Toyko, Japan

[21] Appl. No.: 676,224

[22] PCT Filed: Jan. 25, 1995

[86] PCT No.: PCT/JP95/00085
§ 371 Date: Jul. 23, 1996
§ 102(e) Date: Jul. 23, 1996

[87] PCT Pub. No.: WO95/20388
PCT Pub. Date: Aug. 3, 1995

[30] Foreign Application Priority Data

Jan. 26, 1994 [JP] Japan ................................. 6-007160
Jul. 26, 1994 [JP] Japan ................................. 6-173042

[51] Int. Cl.$^6$ ................................................ A61K 31/51
[52] U.S. Cl. ........................................................ 514/276
[58] Field of Search ............................................ 514/276

[56] References Cited

FOREIGN PATENT DOCUMENTS

WO 92/21368  12/1992  WIPO .

OTHER PUBLICATIONS

Merelr Index 10th Ed 1985 # 9130 & 9131.
Khaled, Mahnoz 1993, 118CA;87649v.
Anderson et al,1983, 99 CA193593w.

Anderson et al., "Effects of B–Complex Vitamins on Cellular and Humoral Immune Functions in vitro and in vivo", pp. 77–84, Immunology Section, Dept. Medical Microbiology. Institute of Pathology, University of Pretoria, Pretoria, Republic of S. Africa.

Kirk–Othmer, "Encyclopedia of Chemical Technology: Vitamins to Zone Refining", vol. 24, Third Edition, pp. 124–139, 1984.

*Primary Examiner*—Russell Travers
*Attorney, Agent, or Firm*—Oblon, Spivak, McClelland, Maier & Neustadt, P.C.

[57] ABSTRACT

An anti-HIV agent, an anti-HIV effect-potentiating agent and a prophylactic and remedial agent for AIDS each comprising, as an active ingredient, a vitamin $B_1$ derivative such as thiamine disulfide, bisbentiamine, bisbutytiamine, bisibutiamine, alitiamine, fursultiamine or octotiamine, or the salt thereof.

The agents according to the present invention are useful for prophylaxis of and treatment for AIDS because they have a very preferable nature that they inhibit the growth of HIV without killing cells against primarily infected cells, but exhibit both cell-killing effect and HIV-killing effect at the same time against persistent-production cells which have come to persistently produce HIV.

23 Claims, 4 Drawing Sheets

ANTI-HIV AGENT

This application is a 371 of PCT/JP95/00085 filed Jan. 25, 1995.

TECHNICAL FIELD

The present invention relates to an anti-HIV (Human Immunodeficiency Virus) agent useful for prophylaxis of and treatment for Acquired Immune Deficiency Syndrome (AIDS), and an anti-HIV effect-potentiating agent.

BACKGROUND ART

AIDS is a disease caused by HIV infection, and the number of patients thereof is rapidly increasing since this disease was discovered in the United States of America in 1983. It has been known to use azidothymidine (AZT), didanosine (DDI) or the like, which is an anti-HIV agent, in treatment for such AIDS.

However, AZT is recognized to have a life-prolonging effect to a significant extent, but involves a problem that it has side effects such as headache, gastrointestinal disorders and a myelodepresant effect. Besides, since many of these anti-HIV agents, which have heretofore been studied, have been based on the action mechanism that DNA synthesis in the replication process of HIV is inhibited to suppress the proliferation of HIV, they have involved a problem that the DNA synthesis of normal cells is also suppressed at the same time as the inhibition of HIV, and normal cells of a patient hence decrease, and consequently, the patient still more falls into a dangerous condition.

It is accordingly an object of the present invention to provide a remedy for AIDS, which is excellent in safety and efficacy.

DISCLOSURE OF THE INVENTION

In view of the foregoing circumstances, the present inventors have screened anti-HIV effects of various compounds in accordance with a screening method for anti-HIV agents by Tat, which has recently been developed. As a result, it has been found that the following compounds (1) which are widely used as vitamin $B_1$ derivatives, exhibit an anti-HIV effect by an action mechanism which is not found in the existing anti-HIV agents, have an effect of potentiating the effects of other anti-HIV agents and are useful for prophylaxis of and treatment for AIDS, thus leading to completion of the present invention.

Namely, the present invention is directed to an anti-HIV agent comprising, as an active ingredient, a vitamin $B_1$ derivative represented by the following general formula (1):

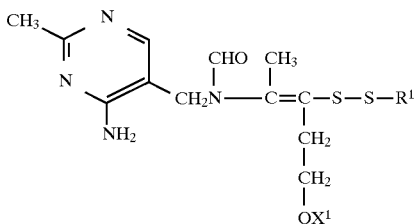

wherein $X^1$ means a hydrogen atom, an acyl group having 1–18 carbon atom or a phosphono group, and $R^1$ denotes an alkenyl group having 2–6 carbon atoms, a tetrahydrofurfuryl group, a 3-acetylthio-7-methoxycarbonylheptyl group or a group represented by the formula (2):

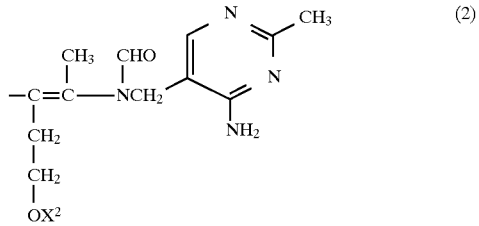

in which $X^2$ means a hydrogen atom, an acyl group having 1–18 carbon atom or a phosphono group, or a salt thereof, and an anti-HIV effect-potentiating agent comprising said compound.

The present invention is also directed to a prophylactic and remedial agent for AIDS, comprising, as an active ingredient, the vitamin $B_1$ derivative or the salt thereof.

The present invention is further directed to use of the vitamin $B_1$ derivative or the salt thereof for an anti-HIV agent, an anti-HIV effect-potentiating agent and a prophylactic and remedial agent for AIDS.

The present invention is still further directed to a method of inhibiting the proliferation of cells persistently infected with HIV, which comprises administering the vitamin $B_1$ derivative or the salt thereof to the cells persistently infected with HIV.

BEST MODE FOR CARRYING OUT THE INVENTION

Figure 1:
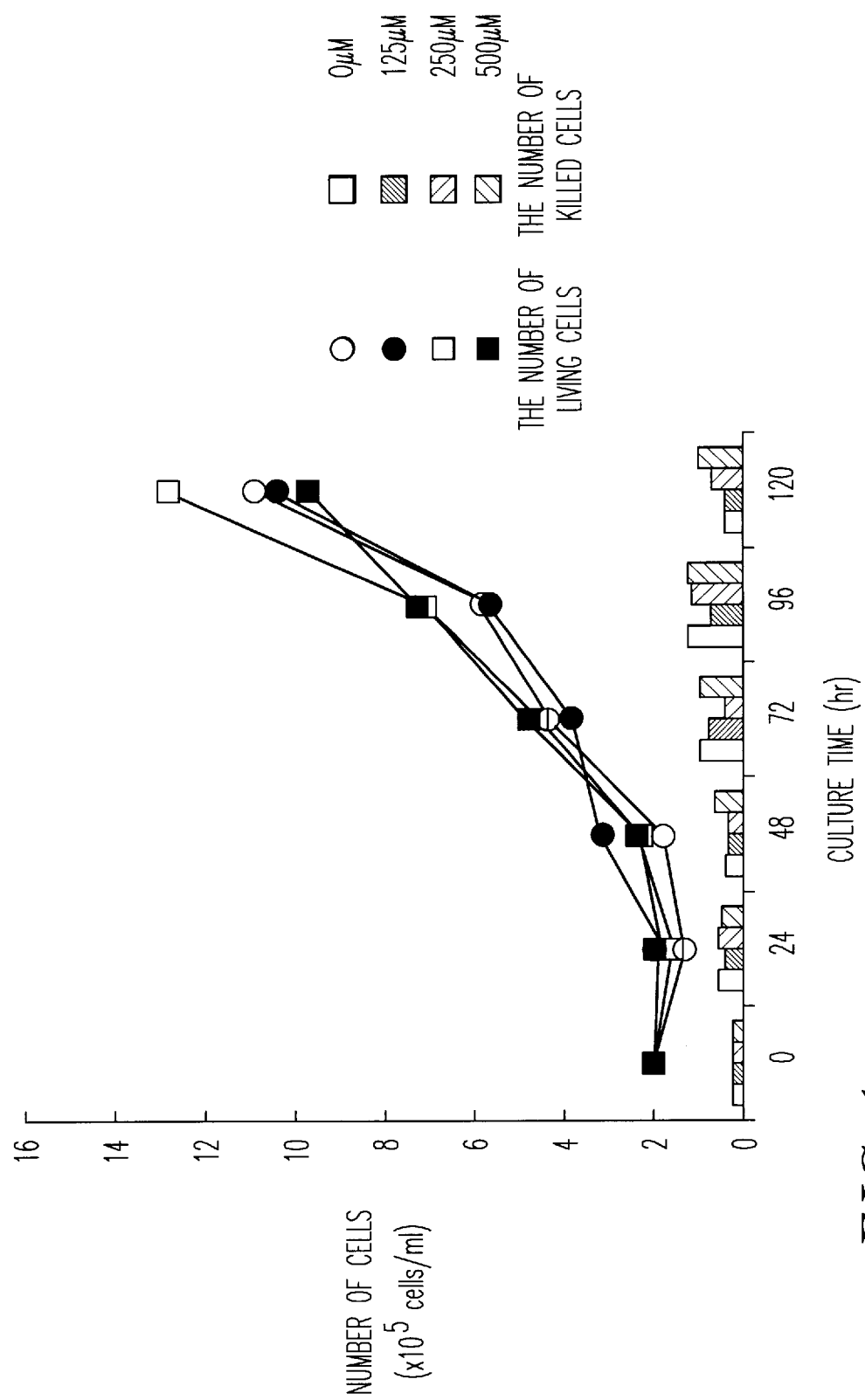
FIG. 1 illustrates the result of an cytotoxicity test of thiamine disulfide against CEM cells.

Examples of the acyl groups represented by $X^1$ and $X^2$ in the general formula (1) and having 1–18 carbon atoms include alkanoyl groups having 1–18 carbon atoms and aroyl groups having 6–10 carbon atoms. Examples of the alkanoyl groups having 1–18 carbon atoms include acetyl, propionyl, butyryl, isobutyryl, pentanoyl, hexanoyl, octanoyl, decanoyl, dodecanoyl, tetradecanoyl, hexadecanoyl and octadecanoyl groups, while examples. Of the aroyl groups include benzoyl and naphthoyl groups. In the case where $X^1$ and $X^2$ are hydrogen atoms, namely, in the form of thiamine disulfide, the compound exhibits an excellent anti-HIV effect as demonstrated in Examples. When any of the exemplified acyl groups is introduced as $X^1$ and $X^2$, it is possible to more enhance the anti-HIV effect when such a compound is applied to a living body.

Examples of the alkenyl group represented by $R^1$ and having 2–6 carbon atoms include vinyl, allyl, 2-butenyl and 2-pentenyl groups, with the allyl group being particularly preferred.

No particular limitation is imposed on the salts of the compounds (1) so far as they are pharmaceutically permissible salts. However, examples thereof include nitrates, hydrochlorides, acetates and sulfates.

Preferable examples of the compounds (1) or the salts thereof useful in the practice of the present invention include thiamine disulfide, thiamine disulfide nitrate, thiamine disulfide phosphate, bisbentiamine, bisbutytiamine, bisibutiamine, alitiamine, fursultiamine and octotiamine. Of these, thiamine disulfide is particularly preferred.

The anti-HIV agent or a prophylactic and remedial agent for AIDS according to the present invention is obtained by suitably adding medicinal carriers such as an excipient, binder, lubricant, disintegrator, coating, emulsifier, suspension, solvent, stabilizer, absorbefacient, ointment base or the like to the compound (1) or the salt thereof as needed, or forming a liposome thereof, thereby preparing a drug composition in the form for oral administration, injection administration, intrarectal administration or the like in accordance with a method known per se in the art.

In the case where the compound (1) or the salt thereof is used as an agent for potentiating the anti-HIV effect, it is used in combination with other compounds exhibiting an anti-HIV effect.

Examples of the other anti-HIV agents include, to say nothing of azidothymidine and didanosine which have already been clinically used, drugs on their way to development as anti-HIV agents at present, namely, soluble CD4, polysaccharide sulfates and T22 which prevent the adsorption, membrane fusion and invasion of virus; a shelling substance, bicyclam; dideoxynucleoside drugs, non-nucleoside inhibitors, suramin and the like which act on reverse transcriptases; anti-sense oligonucleotides, ribozymes, rev inhibitors and the like which act on an expression system; and protease inhibitors, glycolation inhibitors and interferon.

The preparation for the oral administration may preferably be in the form of a granule, tablet, sugar-coated tablet, capsule, soft capsule, pill, solution, emulsion, suspension or the like; the preparation for the injection administration may preferably be in the form for intravenous injection, intramuscular injection, subcutaneous injection, or drip injection or the like; and the preparation for the intrarectal administration may preferably be in the form of a suppository, capsule or the like.

The dose of such a preparation varies according to administration route, the age and condition of the patient to be dosed, and the like. However, it is preferable that the dose be generally 1–1,000 mg per day for an adult in terms of the compound (1) or the salt thereof. This amount of the preparation is dosed once or in portions.

EXAMPLES

The present invention will hereinafter be described in more detail by the following examples. However, the present invention is not limited to these examples.

Example 1

Tat-inhibiting Effect

After a reporter plasmid and an activator plasmid of Tat were cotransfected into COS-7 cells by a DEAE dextran method to culture the cells at 37° C. for 24 hours in the presence of 5% $CO_2$, the transfectant was added to 96-well microplates, in which a test agent had been placed in advance, in a proportion of $1 \times 10^4$ cells/well, followed by reculture at 37° C. for 3 days in the presence of 5% $CO_2$. A supernatant (50 μl) of each of the cultures was then added to another 96-well microplate in which p-nitrophenyl phosphate as a substrate and a buffer had been placed, followed by incubation at 37° C. for 3 hours. The variation in absorbance at 405 nm due to p-nitrophenol formed was then measured to determine the presence of a Tat-inhibiting effect. The results are shown in Table 1.

TABLE 1

| Name of agent | Concentration (μM) | Specific activity (%) (Average ± SE) |
|---|---|---|
| Control (culture supernatant) | — | 100 |
| Glutathione | 250 | 109.5 ± 17.0 |
| N-Acetylcysteine | 500 | 81.5 ± 5.7 |
|  | 250 | 92.0 ± 8.0 |
|  | 125 | 106.9 ± 13.0 |
| α-Lipoic acid | 250 | 17.5 ± 2.1 |
|  | 125 | 41.6 ± 9.9 |
|  | 62.5 | 78.8 ± 7.4 |
| Thiamine disulfide | 500 | 36.1 ± 6.3 |
|  | 250 | 64.4 ± 6.1 |
|  | 125 | 92.3 ± 6.1 |

As apparent from Table 1, thiamine disulfide inhibited the activity of Tat in dependence on dose at concentrations of 125–500 μM.

Example 2

Cytotoxicity Test

Figure 2:
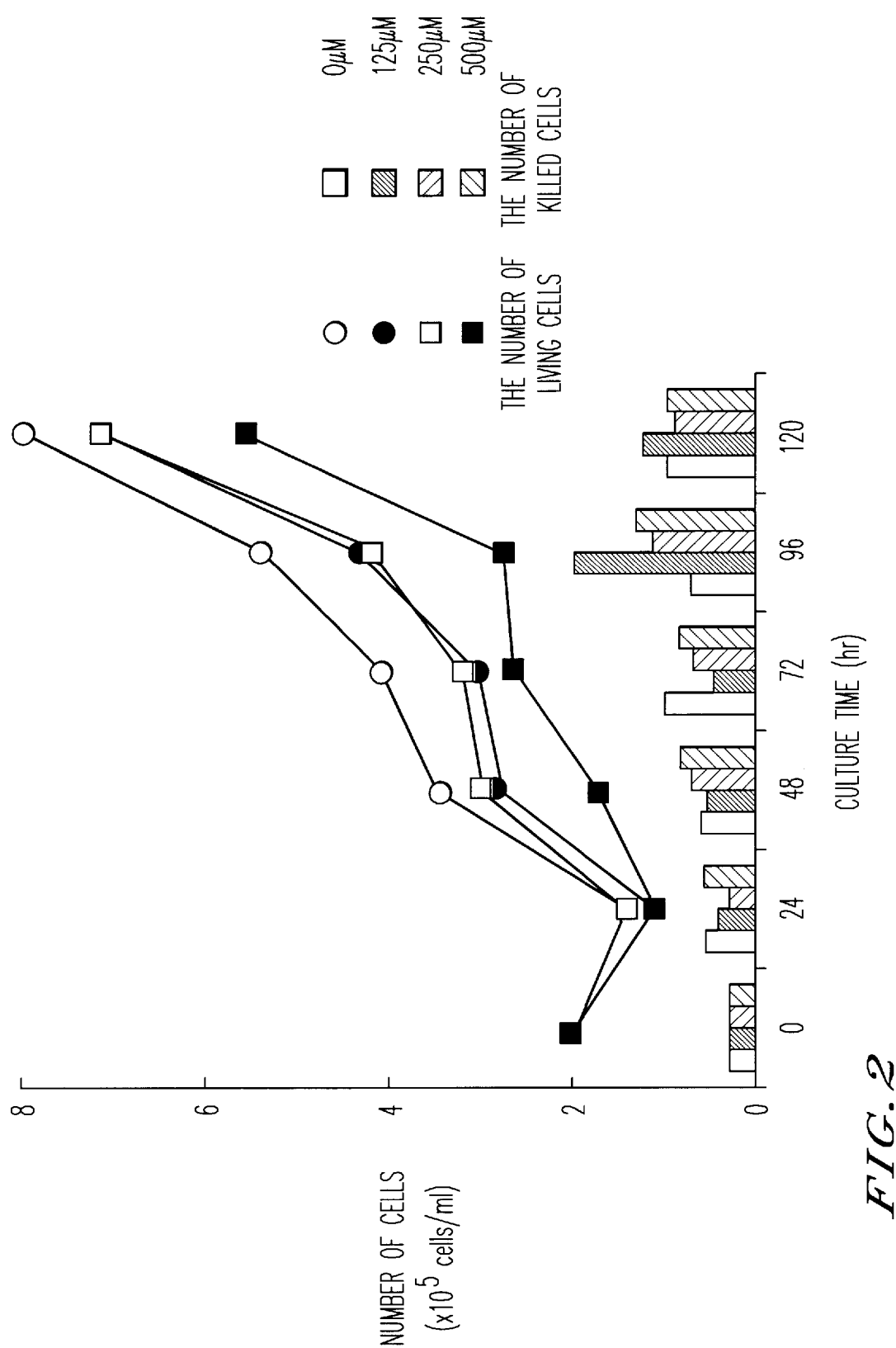
FIG. 2 illustrates the result of an cytotoxicity test of thiamine disulfide against CEM/LAV cells.

Culture solutions (10 ml) of CEM and a strain CEM/LAV persistently producing HIV-1, both, in a logarithmic growth phase were prepared with media containing various concentrations of a test agent so as to give a concentration of $2.5 \times 10^5$ cells/ml, followed by culture at 37° C. in the presence of 5% $CO_2$. After pipetting each cells culture solution every 24 hours, it was collected to count the number of living cells and the number of killed cells by a trypan blue dye exclusion test. As a result, as illustrated in FIGS. 1 and 2, thiamine disulfide did not affect the growth and proliferation of the CEM cells at concentrations not greater than 500 μM, and clearly inhibited the growth and proliferation of the CEM/LAV cells persistently producing HIV-1 at a concentration of 500 μM. However, the number of killed cells did not increase.

Example 3

Detection of HIV-constituting Proteins by Primarily Infected CEM Cells

Cells were collected from a culture solution ($1.0 \times 10^6$ cells/ml, 108 ml) of CEM in a logarithmic growth phase by centrifugation (260×g, 5 minutes). An HIV-1 virus solution ($12 \times 10^5$ $TCID_{50}$) was added to the cells to culture them at 37° C. for 24 hours in 180 ml of a medium, thereby adsorbing the virus thereon. After a culture supernatant containing the virus was then removed by centrifugation (260×g, 5 minutes), and the residue was washed three times with 50 ml of an RPMI-1640 basal medium under centrifugation (260×g, 5 minutes), media separately containing predetermined concentrations of test agents were used to prepare cell suspensions ($1 \times 10^5$ cells/ml, 50 ml×2 sample for each concentration of the test agents). Each of these cell culture solutions was collected in 25-ml portions every 24 hours until 96 hours passed by. The collected solutions were subjected to SDS-PAGE, followed by western immunoblotting to detect virus-constituting proteins. Incidentally, an HIV-1 positive serum was used as a primary antibody.

Figure 3:
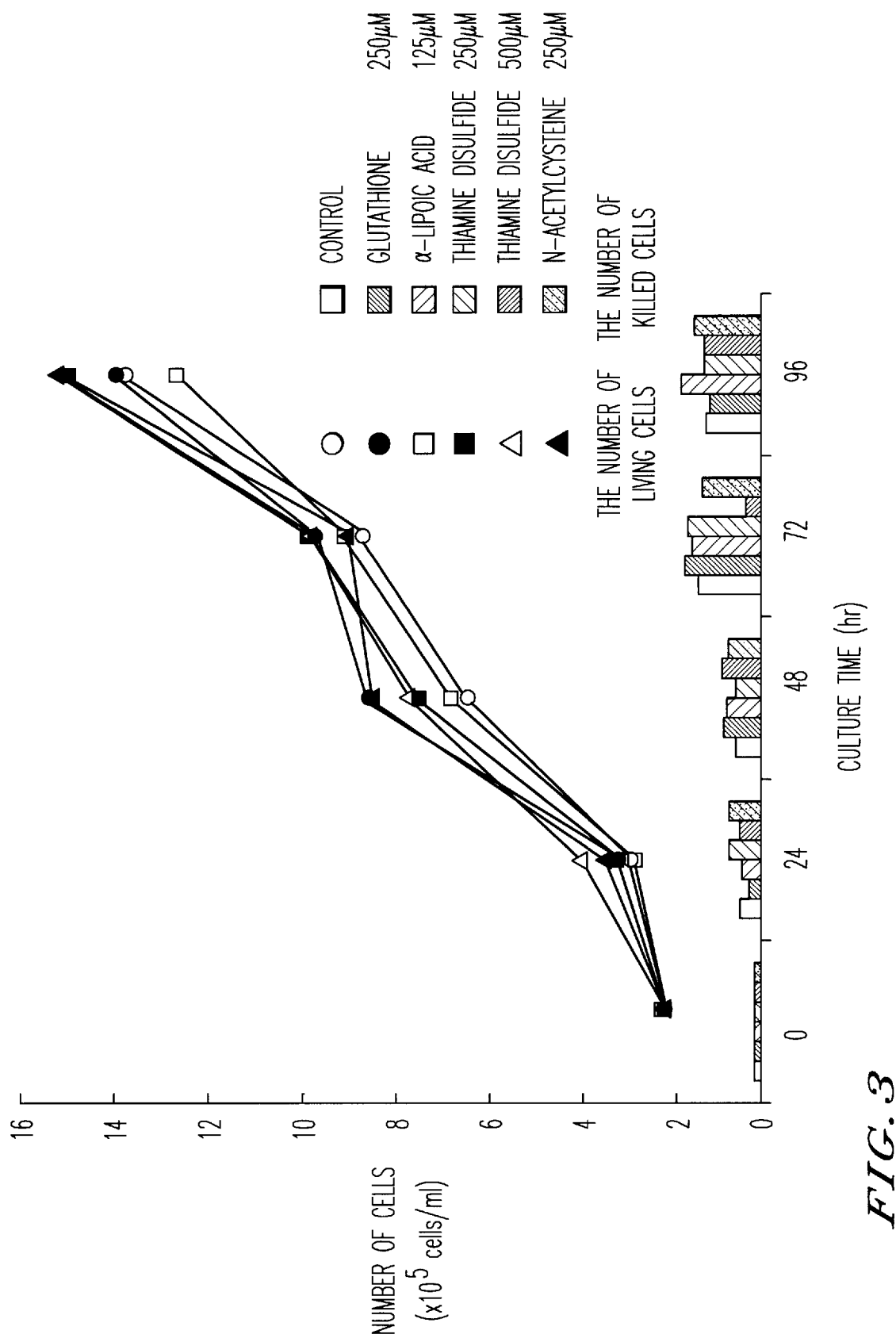
FIG. 3 illustrates an effect of thiamine disulfide on the proliferation of primarily infected CEM cells.
Figure 4:
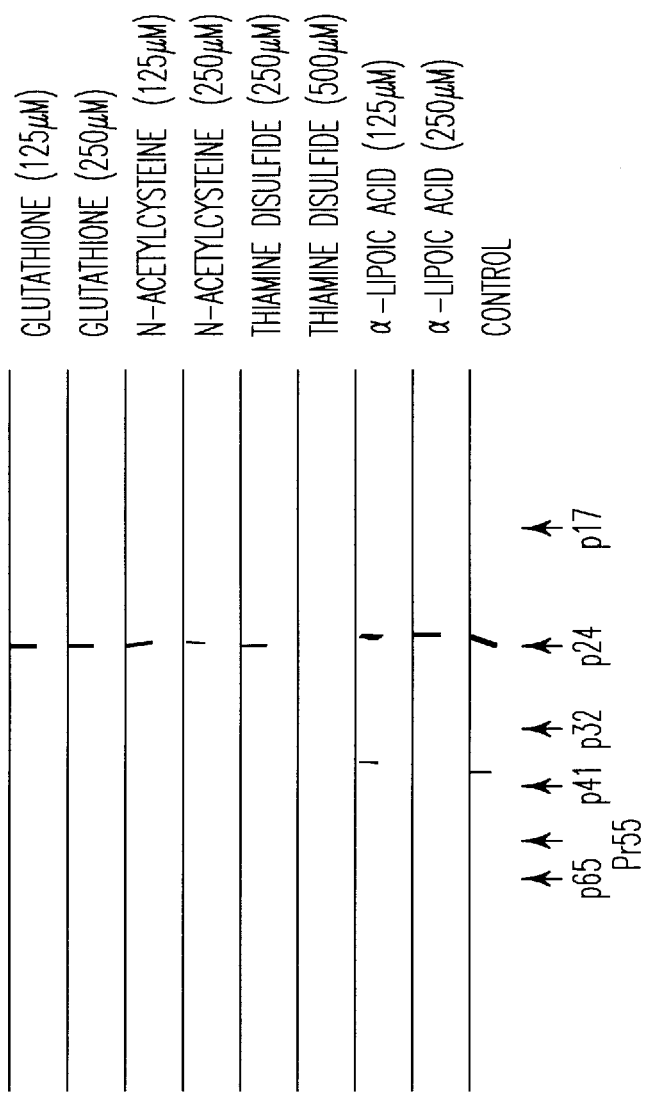
FIG. 4 illustrates the result of the detection of HIV-constituting proteins in the addition of thiamine disulfide by western immunoblotting.

Effects on the cell growth of the primarily infected CEM cells are illustrated in FIG. 3, while the results of the detection of HIV-constituting proteins are shown in FIG. 4. As a result, it was found that thiamine disulfide did not affect the growth of the primarily infected CEM cells at concentrations not greater than 500 μM. However, it was further revealed that a viral infectious titer in a supernatant of the culture solution containing 500 μM of thiamine disulfide was 0.3% of a control, and neither p24 protein nor p41 protein was formed in the culture supernatant. Namely, this means that HIV is scarcely formed in spite of the growth of the infected cells.

Example 4
Anti-HIV Activity

Predetermined concentrations of test agents were separately added to cells ($2\times10^5$ cells/ml, 10 ml) persistently infected with HIV in a logarithmic growth phase to culture them for 96 hours, thereby counting the number of living cells and the number of killed cells every 24 hours by a trypan blue dye exclusion test to determine the cytotoxic effects of the test agents on the cells. A viral infectious titer ($TCID_{50}$/ml) in each of the culture solutions incubated for 96 hours was determined by 72-hour culture using, as an index, the giant cell formation of MT-4 cells. As a control, culture was conducted in a medium free of any agent. An anti-HIV activity (inhibition %) was determined in accordance with the following equation.

Anti-HIV activity (inhibition %) =

$$\frac{TCID_{50}/\text{ml of agent-treated group}}{TCID_{50}/\text{ml of control}} \times 100$$

As a result, as shown in Table 2, thiamine disulfide exhibited marked anti-HIV activities against CEM/LAV-1, $H_9$/MN and Molt-4/IIIB cells, which persistently produced HIV, at a concentration of 500 $\mu$M, and its inhibition effect was 90–98%. Thiamine disulfide also exhibited marked anti-HIV activities against $U_{937}$/RF cells. Fursultiamine exhibited marked anti-HIV activities against CEM/LAV-1, $H_9$/MN and $U_{937}$/RF cells at a concentration of 50 $\mu$M, while alitiamine exhibited marked anti-HIV activities against CEM/LAV-1 cells at a concentration of 50 $\mu$M. Bisibutiamine also exhibited marked anti-HIV activities against $H_9$/MN cells at a concentration of 50 $\mu$M. All these compounds were not recognized to have a cytotoxic effect at the above concentrations.

TABLE 2

| | Anti-HIV activities (inhibition %) | | | |
|---|---|---|---|---|
| | Infected cell | | | |
| Agent ($\mu$M) | CEM/LAV-1 | $H_9$/MN | Molt-4/IIIB | $U_{937}$/RF |
| Control 0 | 0 | 0 | 0 | 0 |
| Thiamine disulfide | | | | |
| 125 | 51 | 90 | 80 | 0 |
| 500 | 90 | 99 | 97 | 80 |
| Fursultiamine 50 | 95 | 96 | 0 | 60 |
| Alitiamine 50 | Selective effect | 0 | 0 | 0 |
| Bisibutiamine 0 | 0 | 60 | 0 | 0 |

INDUSTRIAL APPLICABILITY

The compounds (1) or the salts thereof exhibit HIV-inhibiting action as a Tat-inhibiting effect and a proliferation-inhibiting effect on HIV in cells which persistently produce HIV and inhibit the production of viral proteins without exhibiting cell inhibition against primarily infected cells. More specifically, they have a very preferable nature that they inhibit the growth of HIV without killing cells against primarily infected cells, but exhibit both cell-killing effect and HIV-killing effect at the same time against persistent-production cells which have come to persistently produce HIV.

The compounds (1) or the salts thereof also have a nature that they inhibit the replication process of HIV like other anti-HIV substances, and besides have a unique merit of inhibiting viral multiplication without killing any primarily infected cells, to say nothing of normal cells.

Further, the compounds (1) or the salts thereof are agents well known as being free of side effects and high in safety because they are clinically widely used as vitamin $B_1$ derivatives.

Accordingly, the anti-HIV agents according to the present invention, comprising, as an active ingredient, the compound (1) or the salt thereof, and the anti-HIV effect-potentiating agents according to the present invention, comprising said compound are useful for prophylaxis of and treatment for AIDS.

We claim:

1. A method of treating a patient infected with a human immunodeficiency virus (HIV) in need of treatment, comprising administering to the patient an effective amount of a composition comprising an anti-HIV agent represented by formula (1) or a salt thereof:

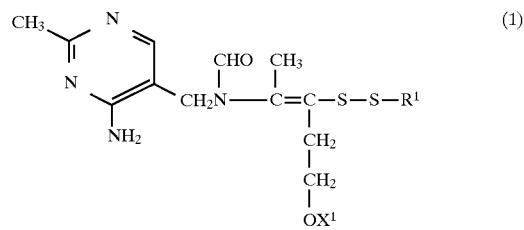

wherein $X^1$ is a hydrogen atom, an acyl group having 1–18 carbon atoms or a phosphono group, and $R^1$ is an alkenyl group having 2–6 carbon atoms, a tetrahydrofurfuryl group, a 3-acetylthio-7-methoxycarbonylheptyl group or a group represented by formula (2):

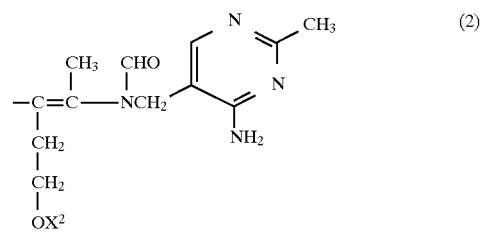

in which $X^2$ is a hydrogen atom, an acyl group having 1–18 carbon atom or a phosphono group.

2. The method of claim 1, wherein the anti-HIV agent represented by formula (1) is selected from the group consisting of thiamine disulfide, thiamine disulfide nitrate, thiamine disulfide phosphate, bisbentiamine, bisbutytiamine, bisibutiamine, alitiamine, fursultiamine and octotiamine.

3. The method of claim 1, wherein the anti-HIV agent represented by formula (1) is thiamine disulfide or a salt thereof.

4. The method of claim 1, wherein the composition further comprises an additional anti-HIV agent.

5. The method of claim 1, wherein 1 to 1,000 mg of the anti-HIV agent represented by formula (1) or a salt thereof is administered to the patient.

6. The method of claim 1, wherein the anti-HIV agent represented by formula (1) or a salt thereof is the sole anti-HIV agent administered to the patient.

7. A method of inhibiting the replication of a human immunodeficiency virus (HIV) in a patient infected with the HIV, comprising administering to the patient an effective amount of a composition comprising an anti-HIV agent represented by formula (1) or a salt thereof:

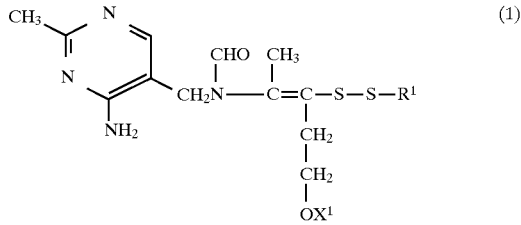

wherein $X^1$ is a hydrogen atom, an acyl group having 1–18 carbon atoms or a phosphono group, and $R^1$ is an alkenyl group having 2–6 carbon atoms, a tetrahydrofurfuryl group, a 3-acetylthio-7-methoxycarbonylheptyl group or a group represented by formula (2):

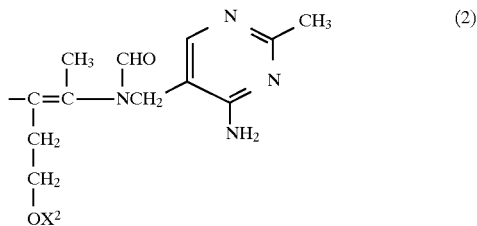

in which $X^2$ is a hydrogen atom, an acyl group having 1–18 carbon atom or a phosphono group.

8. The method of claim 7, wherein the anti-HIV agent represented by formula (1) is selected from the group consisting of thiamine disulfide, thiamine disulfide nitrate, thiamine disulfide phosphate, bisbentiamine, bisbutytiamine, bisibutiamine, alitiamine, fursultiamine and octotiamine.

9. The method of claim 7, wherein the anti-HIV agent represented by formula (1) is thiamine disulfide or a salt thereof.

10. The method of claim 7, wherein the composition further comprises an additional anti-HIV agent.

11. The method of claim 7, wherein 1 to 1,000 mg of the anti-HIV agent represented by formula (1) or a salt thereof is administered to the patient.

12. The method of claim 7, wherein the anti-HIV agent represented by formula (1) or a salt thereof is the sole anti-HIV agent administered to the patient.

13. A method of treating a patient afflicted with acquired immune deficiency disorder (AIDS), comprising administering to the patient an effective amount of a composition comprising anti-HIV agent represented by formula (1) or a salt thereof:

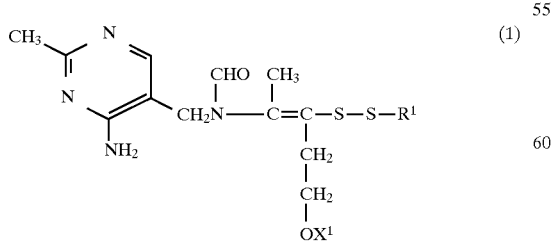

wherein $X^1$ is a hydrogen atom, an acyl group having 1–18 carbon atoms or a phosphono group, and $R^1$ is an alkenyl group having 2–6 carbon atoms, a tetrahydrofurfuryl group, a 3-acetylthio-7-methoxycarbonylheptyl group or a group represented by formula (2):

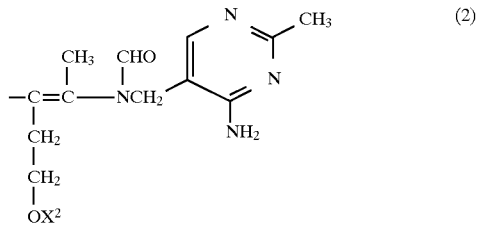

in which $X_2$ is a hydrogen atom, an acyl group having 1–18 carbon atom or a phosphono group.

14. The method of claim 13, wherein the anti-HIV agent represented by formula (1) is selected from the group consisting of thiamine disulfide, thiamine disulfide nitrate, thiamine disulfide phosphate, bisbentiamine, bisbutytiamine, bisibutiamine, alitiamine, fursultiamine and octotiamine.

15. The method of claim 13, wherein the anti-HIV agent represented by formula (1) is thiamine disulfide or a salt thereof.

16. The method of claim 13, wherein the composition further comprises an additional anti-HIV agent.

17. The method of claim 13, wherein 1 to 1,000 mg of the anti-HIV agent represented by formula (1) or a salt thereof is administered to the patient.

18. The method of claim 13, wherein the anti-HIV agent represented by formula (1) or a salt thereof is the sole anti-AIDS agent administered to the patient.

19. A composition for treating patients infected with a human immunodeficiency virus (HIV), comprising:
(a) a first anti-HIV agent represented by formula (1) or a salt thereof:

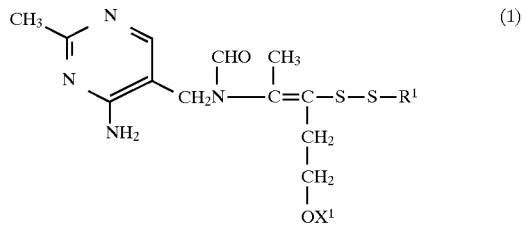

wherein $X^1$ is a hydrogen atom, an acyl group having 1–18 carbon atoms or a phosphono group, and $R^1$ is an alkenyl group having 2–6 carbon atoms, a tetrahydrofurfuryl group, a 3-acetylthio-7-methoxycarbonylheptyl group or a group represented by the formula (2):

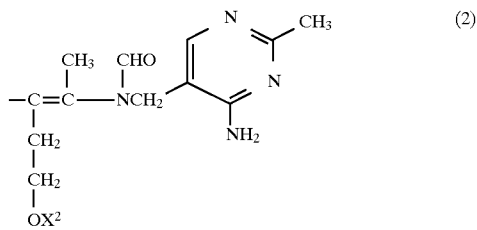

in which $X^2$ is a hydrogen atom, an acyl group having 1–18 carbon atoms or a phosphono group; and
(b) a second anti-HIV agent.

20. The composition of claim 19, wherein the anti-HIV agent represented by formula (1) is selected from the group consisting of thiamine disulfide, thiamine disulfide nitrate, thiamine disulfide phosphate, bisbentiamine, bisbutytiamine, bisibutiamine, alitiamine, fursultiamine and octotiamine.

21. The method of claim 19, wherein the anti-HIV agent represented by formula (1) is thiamine disulfide or a salt thereof.

22. The method of claim 19, wherein the second anti-HIV agent is selected from the group consisting of azidothymidine (AZT), didanoside (DDI), soluble CD4, a polysaccharide sulfates, T22, bicyclam, suramin, antisense oliogonulceotides, ribozymes, rev inhibitors, protease inhibitors, glycolation inhibitors and interferon.

23. The method of claim 19, wherein 1 to 1,000 mg of the compound of formula (1) or a salt thereof is administered to the patient.

* * * * *